United States Patent
Baco et al.

(10) Patent No.: US 6,275,775 B1
(45) Date of Patent: Aug. 14, 2001

(54) METHOD FOR DETERMINING AT LEAST ONE PHYSICO-CHEMICAL PROPERTY OF A PETROLEUM FRACTION

(75) Inventors: Franck Baco, Millery; Alain Quignard, Roussillon; Raymond Szymanski, Montesson la Borde, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/247,332

(22) Filed: Feb. 10, 1999

(30) Foreign Application Priority Data

Feb. 10, 1998 (FR) .................................................. 98 01523

(51) Int. Cl.$^7$ .................................................. G01N 31/00
(52) U.S. Cl. .............................. 702/25; 702/24; 702/30; 436/161; 436/174
(58) Field of Search ........................ 702/22, 24–25, 702/30, 50; 436/29, 60, 139, 161, 174

(56) References Cited

U.S. PATENT DOCUMENTS 4,772,561 * 9/1988 Genshaw ............................. 436/169
4,971,915 * 11/1990 Schwartz et al. .................... 436/161
5,121,337 * 6/1992 Brown .................................. 702/28
5,699,269 * 12/1997 Ashe et al. ........................... 702/30

OTHER PUBLICATIONS

K. Seinsche et al., vol. 112, No. 6, Jun. 1996, pp. 261–263.

* cited by examiner

Primary Examiner—Kamini Shah
Assistant Examiner—Bryan Bui
(74) Attorney, Agent, or Firm—Millen White Zelano & Branigan (57) ABSTRACT

A method for determining at least one physico-chemical property of a petroleum fraction is described in which a conventional analysis of the property is done for a reference petroleum sample set; each reference sample is analyzed by gas chromatography coupled with an atomic emission detector (GC-AED) to determine the distribution of an element from the group of carbon, hydrogen, sulfur, and nitrogen, as a function of the boiling points of the components of the sample, and the coefficients of the correlative model are determined from all of the data. The petroleum fraction whose property is to be determined is analyzed by chromatography under the same conditions, and the data that are obtained are multiplied by the coefficients of the model to determine the value of said property as a function of the boiling points of its components. Application to the determination of the cetane number as a function of the distillation profile of the components of the petroleum fraction.

16 Claims, 5 Drawing Sheets

—— Analysis of the Narrow Fractions  ━━ AED Analysis  ——— AED Simulated Distillation

METHOD FOR DETERMINING AT LEAST ONE PHYSICO-CHEMICAL PROPERTY OF A PETROLEUM FRACTION

The invention relates to an analytical method that makes it possible to quickly predict a set of global physico-chemical properties and/or a temperature profile on complex petroleum products by using a combination of chromatography coupled to specific detectors.

BACKGROUND OF THE INVENTION

The technological background is illustrated by Patents U.S. Pat. Nos. 5,699,269, 4,971,915 and by the publication by SEINSCHEK et al. "Anwendung Der PLS-Regressions Methode Auf Daten der Gaschromatographie Und Der Ir-Spektroskopie [Use of PLS Regression Methods on Gas-Chromatography and IR-Spectroscopy Data] Quality Control of Jet Fuels—PLS Regression Analysis of Gas-Chromatographic and Ir-Spectroscopic Data," Erdoel Erdgas Kohle, Vol. 112, No. 6, June 1996, pages 261–263 XP000641535).

Traditionally, the analytical methods that relate to determining petroleum properties in hydrocarbons take a long time to carry out and are thus very time-consuming. Petroleum products consist of thousands of compounds. These products are thus generally identified and classified based on some of the properties, such as, for example: the range of distillation, density, and the cetane number.

Gas chromatography has been used to predict petroleum properties in gasoline-type petroleum products. Crawford and Hellmuth, Fuel, 1990, 69, 443–447, describe a chromatographic analysis that is able to predict the octane numbers of various effluents that come from the refinery, by application of mathematical models that are based on the statistical technique of principal component regression (PCR). Japanese Patent JP 03-100463 relates to a method that makes it possible to predict the cetane number from a specific analysis by coupling gas chromatography to mass spectrometry. The predicted cetane number is calculated by multilinear regression from the intensities of the selective ions.

These methods are therefore able to determine a global property of a product that contains hydrocarbon, but they are not suitable for providing data on this property as a function of the boiling points of the components of the product.

SUMMARY OF THE INVENTION

Currently, it would be advantageous, and this is an object of the invention, to have an analytical method that is able to predict from various analytical data a set of petroleum properties (or determinations) that are both global and reflect a distillation profile. For this purpose, the techniques of coupling chromatography to specific detectors are the most promising avenues.

These coupling techniques can be gas chromatography coupled either to mass spectrometry or to a flame ionization detector or to specific detectors of sulfur or nitrogen. The coupling of gas chromatography and an atomic emission detector has been preferred to these techniques because of the ease of implementation of this approach, which makes it possible to output the value of at least one element that is selected from the group of carbon, hydrogen, sulfur, and nitrogen, and preferably hydrogen or carbon, as a function of the temperature profile.

Upon further study of the specification and appended claims, further objects and advantages of this invention will become apparent to those skilled in the art.

The invention relates to an analytical method that is able to predict a set of data that consist of global petroleum properties and/or a boiling point profile of petroleum products, from correlative mathematical models.

For this purpose, it is possible:

a) to define a set of petroleum properties and characterizations that can be predicted from analyses that are obtained by coupling;

b) to select the largest possible set of reference petroleum samples that constitute the calibration base, on which will be determined, according to conventional analytical methods, the various petroleum properties and determinations which will be predicted from the results of the coupling;

c) to follow the following analytical approach:

(1) to analyze each of the reference petroleum samples according to the conventional analytical methods that are known to one skilled in the art. The analytical results for each of the determinations will constitute a block Y of, for example, the calculation matrix for producing various correlative models;

(2) to inject the standard products in order to calibrate the various analytical channels of the coupling device under dynamic analysis conditions (calibration of the responses of carbon, hydrogen, sulfur, and nitrogen);

(3) to inject a known n-alkane mixture under the defined analytical conditions in order to determine the relation that links the retention time of these n-alkanes to their boiling points, (4) to inject each of the reference petroleum samples that constitute the calibration base under the same analytical conditions by recording the signals of different channels, with those relating to carbon and hydrogen being preferred, (5) to process the signals of different channels;

(6) to create a base of results that come from processing signals of various analytical channels (%C, %H, %S, %N, . . . , boiling point) that would constitute a block X of, for example, the correlative matrix;

(7) to analyze the various analytical data according to the various multivaried methods of analysis such as partial least square regression, principal component regression, the topological approach, neural nets, to determine the different coefficients of the correlative models.

(d) for the treatment of an unknown petroleum fraction, to follow the procedure of c(2) to c(3) and to inject the sample under the same conditions as c(4), to apply steps c(5) to c(6), (e) to multiply the matrix by the coefficients of the models that are obtained in c(7) to predict the property or set of properties and/or desired determinations.

More specifically, the invention relates to a method for determining at least one physico-chemical property of a petroleum fraction, characterized in that:

a) at least one conventional analysis of a set of reference petroleum samples is carried out to determine the first set of data of a calculation matrix for developing a correlative model;

b) each reference petroleum sample is analyzed by chromatography, coupled to at least one detector under suitable conditions to determine the distribution of at least one element that is selected from the group that is formed by carbon, hydrogen, sulfur, and nitrogen as a function of the boiling points of the components of the sample, and a second set of data of the calculation matrix is drawn up;

c) the different coefficients of the correlative model are determined from the first and second sets of data according to multivaried methods of analysis;

d) chromatographic analysis of said petroleum fraction is done under the same conditions as those of step (b) to determine the distribution of at least one element of the carbon, hydrogen, sulfur, and nitrogen group as a function of the boiling points, and a third set of data relating to the petroleum fraction is drawn up;

e) the third set of data of step (d) is multiplied by the different coefficients of the correlative model; and f) the physico-chemical property that is derived from the petroleum fraction is determined as a function of the boiling points of its components.

The coupling of gas chromatography/atomic emission detector (GC-AED) can be used advantageously for predicting a set of properties as a function of the temperature profile, such as:

physico-chemical characteristics of the product; refraction number, density the elementary composition of the distillation profile the simulated distillation curve of the product (%(m/m)= f(T° C.))

cold properties (pour point, cloud point, for example);

data relating to the concentrations of different radicals and their distribution as a function of the boiling point of the product;

the aniline point the smoke point, the percentage % (m/m) of aromatic carbon Ca;

the percentage % (m/m) of paraffinic carbon Cp;

the percentage % (m/m) of naphthenic carbon Cn;

the cetane number.

All of these determinations are made within a relatively short time (for example on the order of 90 minutes).

It is thus possible to optimize by the method according to the invention the cutpoints of the products in refining and petrochemistry processes as a function of said specifications.

This method makes it possible to predict by the correlative method a set of physico-chemical properties and a certain number of global petroleum characterizations and/or temperature profiles of complex hydrocarbon mixtures from the results of the detailed elementary analysis (as a function of the boiling point) of the petroleum product that is obtained by coupling chromatography, in particular gas chromatography, and detection by a specific detector, preferably by atomic emission (GC-AED).

The chromatography technique that provides for the separation of different components can, however, differ in some cases according to the applications that are used. Liquid chromatography or supercritical fluid chromatography can in some cases be used, as can the separation of different families of saturated, aromatic compounds and polar compounds (resins) by preparative liquid chromatography, followed by analysis of these different fractions by GC-AED.

Capillary column gas chromatography combined with an atomic emission detector, however, remains the most commonly used technique.

Instrument control (chromatography, detector) and the collection of analytical data, as well as their processing, are facilitated by control and operational software.

The petroleum sample is injected into the chromatograph, where the compounds are separated as a function of their boiling points. For this type of analysis, partial separation of the compounds most often proves to be adequate.

Among other things, the analysis makes it possible to determine a set of properties as a function of the boiling point of the product. To do this, preliminary calibration of the analytical chain by the injection of a synthetic hydrocarbon mixture (generally n-alkanes) makes it possible to determine the relation that links the retention time of the reference products to their boiling points.

To carry out a quantitative elementary analysis of the petroleum product, the different analytical channels of the detector (C, H, S, N, etc.) are calibrated either from one or more pure products, or from a reference petroleum product whose elementary analysis is known (circular tests that are carried out with different laboratories, for example).

The technique is generally applicable to all of the products on which chromatography can be used and whose boiling points are less than 700° C.

The totally or partially separated different types are transferred to the detector under dynamic flow conditions that have been previously defined by the analytical method. The chromatographed effluents are atomized in high-energy plasma. When they are de-excited, the atoms emit an atomic emission spectrum that is transmitted to a spectrometer through a window in a measuring chamber in the axis of the plasma. The spectrum that is emitted is separated into characteristic wavelengths that are focused on the detector.

The analytical results (detailed elementary analysis as a function of temperature) and the related properties are recorded in two matrices, to be processed according to the mathematical processing methods that are described below.

The reference values that are obtained according to the conventional techniques on the set of petroleum samples that constitute the calibration base are stored in, for example, a matrix Y. The set of analytical data that comes from GC-AED coupling (T° C., %C, %H, %S, %N, distillation yield, etc . . . ) are stored in, for example, matrix X. The two matrices are subjected to mathematical processing that can be, as appropriate: partial least square (PLS) regression methods, principal component regression (PCR), neural net, the topological approach, to describe the relation that links the properties to the analytical data that come from the GC-AED coupling. The coefficients that are thus determined by the model are multiplied with analytical data from a set of petroleum products for which we want:

a) to predict the desired property/properties;

b) to track the changes of a property or a set of properties during the process (followed by pilot or industrial units).

PLS and PCR statistical methods are described in the literature: Wold, S.; A. Ruhe, H. Wold, and W. J. Dunn, "The Collinearity Problem in Linear Regression," The Partial Least Square (PLS) Technique, "Approach to Generalized Inverses," Siam J. Sci. Stat. Compt., 1984 5(3), 735–743, or Gelaidi, P.; R. B. Kowalski "Partial Least Square" Un aide pédagogique [A Teaching Aid] "Anal. Chim. Acta, 1986, 185, 1–17, or Hökuldson, A., PLS Regression Methods," J. Chemometrics, 1988, 2, 211–228 and other edited articles in the journal such as Journal of Chemometrics or Intelligence Laboratory Systems; Frank, I.; Friedman, J., "A User's Guide to Principal Component," Whiley Interscience, New York, 1991, Montgomery, D. C., "Introduction to Linear Regression Analysis," Whiley Interscience, New York, 1990 and Marlens, H.; Naes, T., "Multivariate Calibration," Whiley Interscience, New York, 1989.

The invention will be better understood based on the following figures, where.

To predict the properties of an unknown distillate, the first step consists in selecting a set of reference distillates on which the set of properties and petroleum characterizations that we want to predict by correlation has been determined according to the reference methods.

Among these products, distillates were selected that come from the catalytic cracking process (catalytic cracking low-test gasoline, Light Cycle Oil and Heavy Cycle Oil), gas oils of diverse origins (atmospheric-distillation gas oils, hydrotreated gas oils, hydrocracking gas oils, visbreaking gas oils, hydrodemetalization gas oils, and hydrorefining gas oils as well as kerosenes of various origins). The list of the different products is indicated in Table 1.

Figure 1:
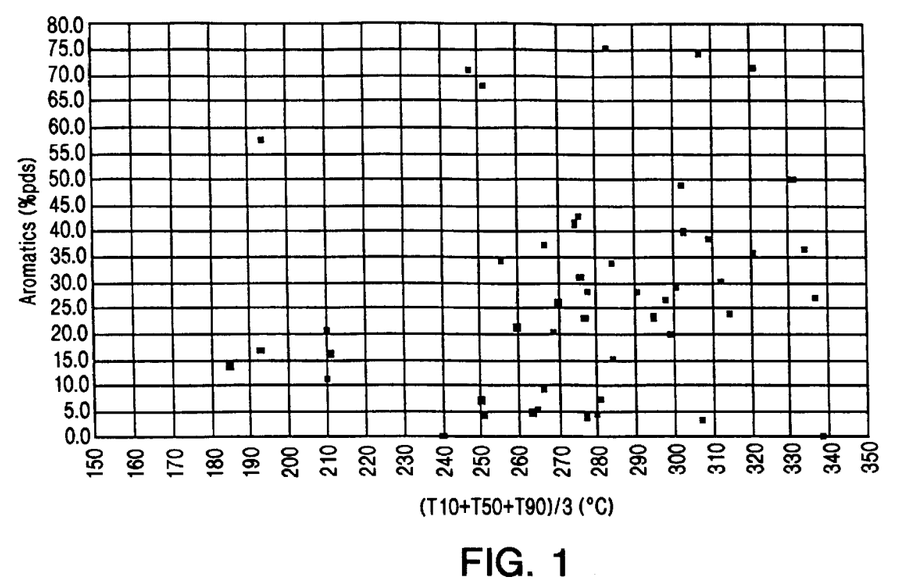
FIG. 1 depicts an example of a sample base, according to the aromatic hydrocarbon content and the mean temperature of the fraction

FIG. 1 shows the area that is covered by the sample base. For this purpose, the total aromatic compound content that is measured by mass spectrometry as a function of the mean boiling point, with the latter being defined as the arithmetic mean of three temperatures that correspond to 10, 50 and 90% of distilled volume according to the ASTM D86 method, has been shown.

The petroleum property prediction and/or characterization method is illustrated by two examples of gas oils that describe the calculation of the cetane number and the % of aromatic-type carbon from the data that come from the coupling, whereby these values can be calculated globally and with a distillation profile. This methodology can be applied to the calculation of a set of properties (and petroleum determinations) that are both physical and chemical on all of the chromatographable petroleum products.

The entire disclosure of all applications, patents and publications, cited above and below, and of corresponding French Application No. 98/01.523, filed Feb. 10, 1998 is hereby incorporated by reference.

TABLE 1

Distillates that Constitute the Calibration Base

| Ref. | Type of Distillate |
|---|---|
| 1 | Atmospheric distillation |
| 2 | atmospheric distillation |
| 3 | hydrotreated |
| 4 | atmospheric distillation |
| 5 | atmospheric distillation |
| 6 | hydrocracking |
| 7 | atmospheric distillation |
| 8 | atmospheric distillation |
| 9 | oligomerization |
| 10 | atmospheric distillation |
| 11 | hydrodemetalization |
| 12 | atmospheric distillation |
| 13 | visbreaking |
| 14 | Light Cycle Oil (FCC) |
| 15 | Heavy Cycle Oil (FCC) |
| 16 | atmospheric distillation |
| 17 | atmospheric distillation kerosene |
| 18 | colza methyl ester |
| 19 | atmospheric distillation kerosene |
| 20 | atmospheric distillation under a vacuum |
| 21 | atmospheric distillation kerosene |
| 22 | atmospheric distillation |
| 23 | FCC low-test gasoline |

TABLE 1-continued

Distillates that Constitute the Calibration Base

| Ref. | Type of Distillate |
|---|---|
| 24 | Light Cycle Oil (FCC) |
| 25 | Light Cycle Oil (low S content) |
| 26 | Light Cycle Oil (FCC) |
| 27 | visbreaking |
| 28 | hydrodemetalization |
| 29 | hydrodemetalization |
| 30 | atmospheric distillation |
| 31 | atmospheric distillation |
| 32 | atmospheric distillation |
| 33 | atmospheric distillation |
| 34 | thermal cracking |
| 35 | atmospheric distillation |
| 36 | heavy thermal cracking gas oils |
| 37 | hydrorefining |
| 38 | hydrorefining |
| 39 | hydrotreated |
| 40 | hydrotreated kerosene |
| 41 | atmospheric distillation |
| 42 | hydrodesulfuration |
| 43 | heavy atmospheric distillation gas oil |
| 44 | hydrotreated |
| 45 | hydrodesulfuration |
| 46 | hydrotreated |
| 47 | hydrocracking |
| 48 | hydrotreated |
| 49 | atmospheric distillation |
| 50 | hydrorefining |

FCC = Fluid Catalytic Cracking

In the foregoing and in the following examples, all temperatures are set forth uncorrected in degrees Celsius; and, unless otherwise indicated, all parts and percentages are by weight.

EXAMPLE 1

Determination of the Global Cetane Number and Distillation Profile

The analytical conditions under which the reference products and those products, some of whose properties are to be predicted, are analyzed are summarized in Tables 2 to 4. If need be, they can be modified for the analysis of a particular product.

TABLE 2

Chromatographic Conditions

| Experimental Parameters | Experimental Conditions |
|---|---|
| Programmed temperature of the injector | |
| Initial temperature | 80° C. |
| Programming speed | 200° C./min |
| Final temperature | 330° C. |
| Duration of the final stage | 51 min |
| Programmed temperature of the furnace | |
| Initial temperature | 60° C. |
| Initial isotherm | 5 min |
| Programming speed | 10° C./min |
| Final temperature | 330° C. |
| Duration of the final stage | 20 min |
| Transfer line temperature | 330° C. |
| Electronic pressure regulator (He) | |
| Initial pressure | 34.5 kPa |
| Duration of the initial stage | 5 min |

TABLE 2-continued

Chromatographic Conditions

| Experimental Parameters | Experimental Conditions |
|---|---|
| Programming speed | 1.4 kPa/min |
| Final pressure | 96.5 kPa |
| Duration of the final initial stage | 2 min |
| Injected volume | 0.5 μl |
| Dilution of the distillate in $CH_2Cl_2$ | 1% volume |

TABLE 3

Atomic Emission Detector Conditions

| | |
|---|---|
| Pressure in the cavity | 10.3 kPa |
| Temperature of the cavity | 330° C. |
| Auxiliary helium gas flow rate | |
| Analysis of distillates | 80 ml/min |
| Analytical lines that are used | |
| Carbon (first injection) | 496 nm |
| hydrogen (first injection) | 486 nm |
| sulfur (second injection) | 181 nm |
| nitrogen (second injection) | 174 nm |
| Supply gas pressure | |
| helium vector gas (N55 grade) | 206.7 kPa |
| Reactant gases | |
| Oxygen pressure (N48 grade) | 151.6 kPa |
| hydrogen pressure (N55 grade) | 379 kPa |
| Duration of the solvent purge | |
| Analysis of the distillates | 3 min |

TABLE 4

Chromatographic Column

| Chromatographic column* | Characteristics |
|---|---|
| CP-Sil-19 CB (Chromopack) Composition | Length: 10 m |
| 7% cyanopropyl 85% methyl and 1% vinylpolysiloxane | Inside diameter: 0.53 mm Outside diameter: 0.70 mm Film thickness: 1 μm Number of theoretical plates: 23,500 |

*An apolar chromatographic column of type DB-1, HP-5, Cpsil-5 can be used equally well.

The elementary analysis of a gas oil by 2% material section (m/m) is given as an example in Table 7 (this breakdown can be modified by sections of 2%, 5%, 10%, 20%, for example). From these variables (yield, T° C., %C, %H, %S, %N, etc.), we can construct matrix X that consists of z variables per sample. The illustration of matrix X is provided in Table 5. It is constructed from a group of reference products (n samples) (calibration base of the model) that are analyzed under the conditions that are described in Tables 2 to 4.

The various petroleum products that constitute the calibration base are further analyzed according to the conventional analytical reference methods (cetane number per CFR engine according to the ASTM D613 method). This series of values constitutes block Y of the calculation matrix, shown in Table 5.

TABLE 5

Block X of the Calculation Matrix (n samples, z variables)

| | | | | |
|---|---|---|---|---|
| $X_{1.1}$ | $X_{1.2}$ | $X_{1.3}$ | ... | $X_{1.2}$ |
| $X_{2.1}$ | $X_{2.2}$ | $X_{2.3}$ | ... | $X_{2.2}$ |
| $X_{3.1}$ | $X_{3.2}$ | $X_{3.3}$ | ... | $X_{3.2}$ |
| " | " | " | | " |
| " | " | " | | " |
| $X_{n.n}$ | $X_{n.2}$ | $X_{n.3}$ | | $X_{n.3}$ |

TABLE 6

Block Y of the Calculation Matrix (n Samples)

$Y_1$
$Y_2$
$Y_3$
"
"
$Y_n$

TABLE 7

Analysis Example Obtained by GC-AED on Distillate 14

| Rdt % | T° C. | % C | % H | % S |
|---|---|---|---|---|
| PI | 149 | 88.3 | 11.70 | 0.041 |
| 2 | 171 | 85.5 | 14.40 | 0.066 |
| 4 | 182 | 87.3 | 12.60 | 0.046 |
| 6 | 189 | 87.0 | 12.90 | 0.036 |
| 8 | 195 | 88.0 | 11.90 | 0.022 |
| 10 | 199 | 87.3 | 12.70 | 0.044 |
| 12 | 203 | 88.6 | 11.40 | 0.020 |
| 14 | 208 | 87.0 | 12.90 | 0.034 |
| 16 | 211 | 87.8 | 12.20 | 0.028 |
| 18 | 214 | 89.2 | 10.70 | 0.024 |
| 20 | 215 | 88.7 | 11.30 | 0.017 |
| 22 | 218 | 88.5 | 11.50 | 0.032 |
| 24 | 222 | 88.6 | 11.40 | 0.027 |
| 26 | 224 | 89.3 | 10.70 | 0.022 |
| 28 | 227 | 87.9 | 12.10 | 0.022 |
| 30 | 230 | 90.0 | 9.95 | 0.030 |
| 32 | 233 | 88.3 | 11.00 | 0.762 |
| 34 | 236 | 88.0 | 11.90 | 0.061 |
| 36 | 239 | 89.0 | 11.00 | 0.038 |
| 38 | 243 | 89.2 | 10.80 | 0.032 |
| 40 | 247 | 87.6 | 12.20 | 0.201 |
| 42 | 249 | 90.3 | 8.93 | 0.750 |
| 44 | 251 | 90.9 | 8.45 | 0.689 |
| 46 | 253 | 89.9 | 9.34 | 0.776 |
| 48 | 256 | 87.7 | 10.90 | 1.350 |
| 50 | 262 | 88.0 | 11.70 | 0.249 |
| 52 | 267 | 87.9 | 11.20 | 0.902 |
| 54 | 269 | 90.3 | 8.80 | 0.854 |
| 56 | 271 | 88.2 | 9.90 | 1.950 |
| 58 | 272 | 91.2 | 8.45 | 0.322 |
| 60 | 276 | 89.1 | 9.38 | 1.540 |
| 62 | 281 | 88.7 | 10.80 | 0.463 |
| 64 | 285 | 88.9 | 9.820 | 1.310 |
| 66 | 288 | 88.5 | 10.30 | 1.130 |
| 68 | 291 | 89.8 | 9.20 | 0.957 |
| 70 | 295 | 88.9 | 10.0 | 1.110 |
| 72 | 299 | 89.3 | 9.89 | 0.819 |
| 74 | 302 | 89.4 | 9.79 | 0.769 |
| 76 | 305 | 90.0 | 9.39 | 0.637 |
| 78 | 310 | 89.0 | 10.30 | 0.707 |
| 80 | 315 | 88.5 | 10.80 | 0.670 |
| 82 | 319 | 90.3 | 9.30 | 0.446 |
| 84 | 324 | 90.0 | 9.60 | 0.412 |
| 86 | 331 | 88.1 | 10.80 | 1.050 |
| 88 | 337 | 89.9 | 9.54 | 0.533 |
| 90 | 344 | 89.5 | 10.00 | 0.500 |
| 92 | 350 | 87.0 | 10.70 | 2.240 |
| 94 | 355 | 90.1 | 9.11 | 0.791 |

TABLE 7-continued

Analysis Example Obtained by GC-AED on Distillate 14

| Rdt % | T° C. | % C | % H | % S |
|---|---|---|---|---|
| 96 | 363 | 86.8 | 10.80 | 2.380 |
| 98 | 373 | 88.2 | 10.1 | 1.75 |
| PF | 409 | 87.2 | 10.9 | 1.88 |

PI = Initial point
PF = Final point

Figure 2:
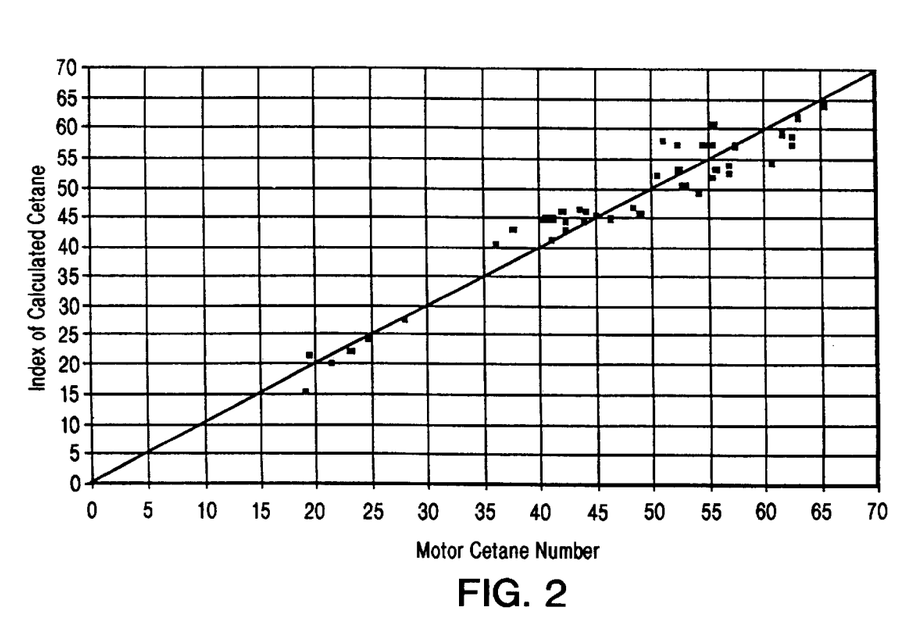
FIG. 2 illustrates the parity diagram of the cetane number FIGS. 3 to 6 how the cetane profiles of different gas oils and their distillation yields as a function of the mean fraction temperature
Figure 3:
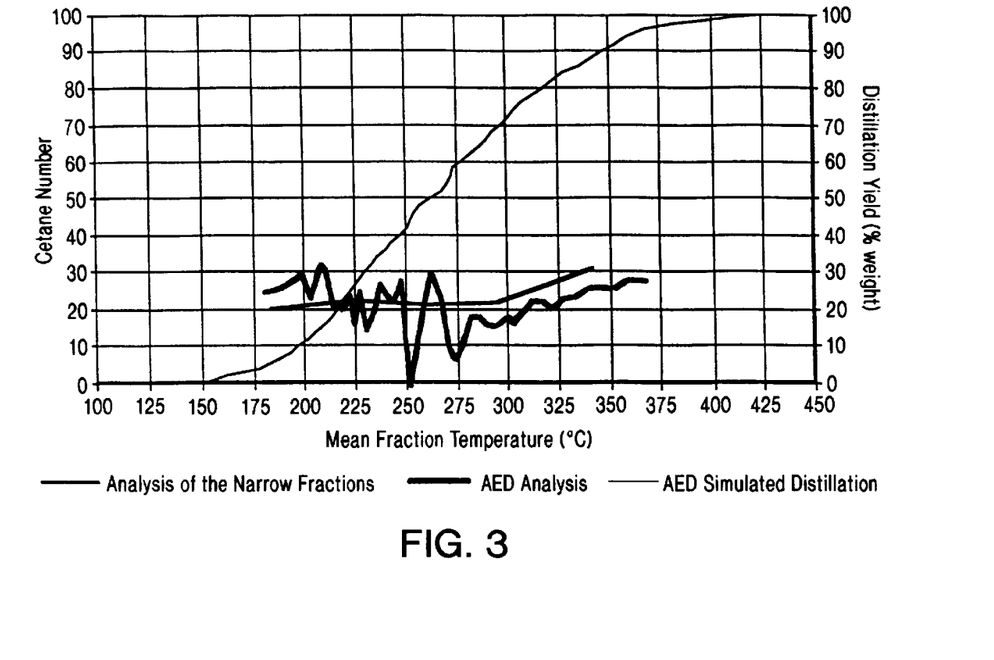
Figure 4:
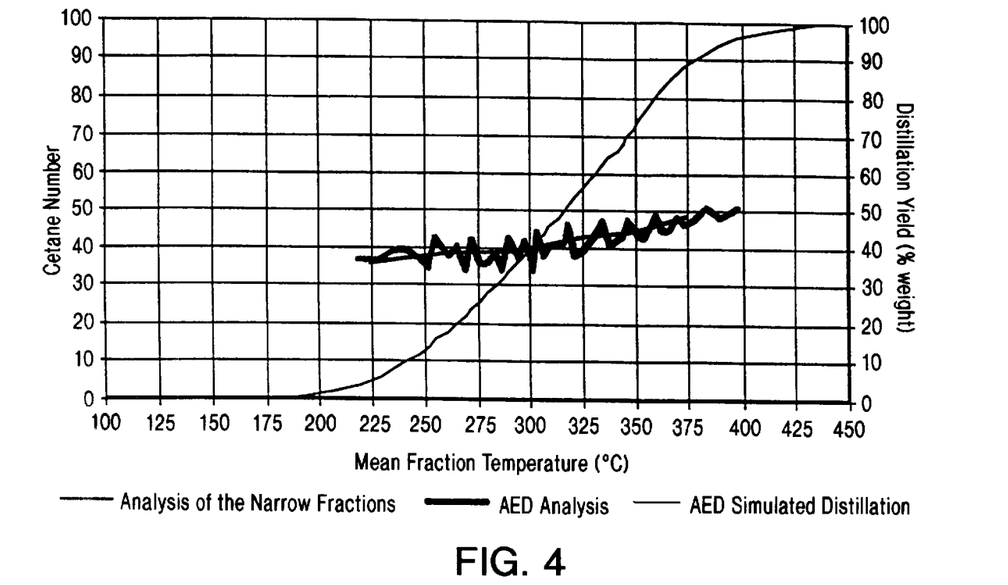
Figure 5:
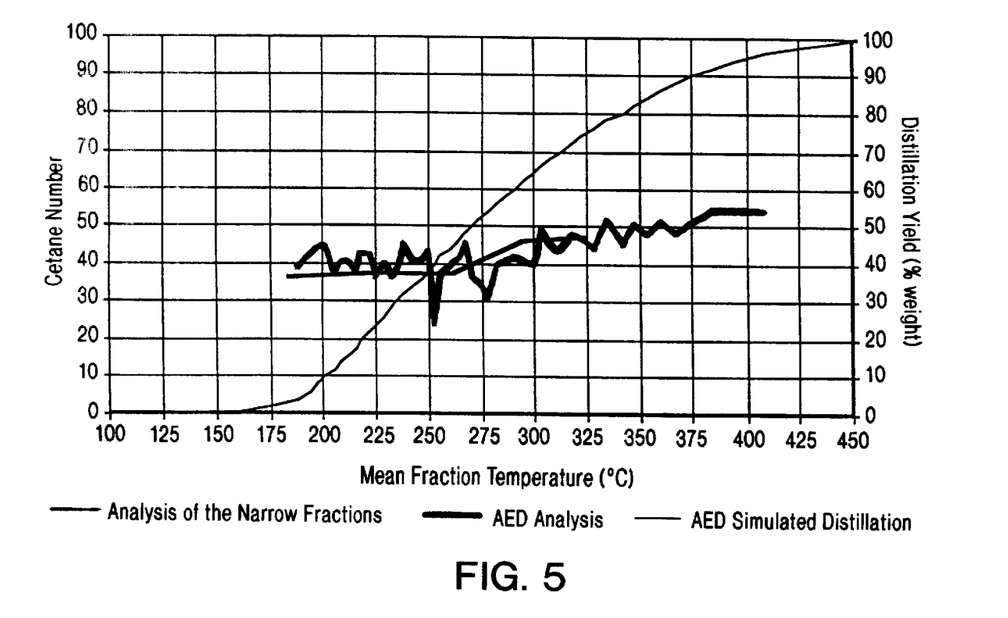
Figure 6:
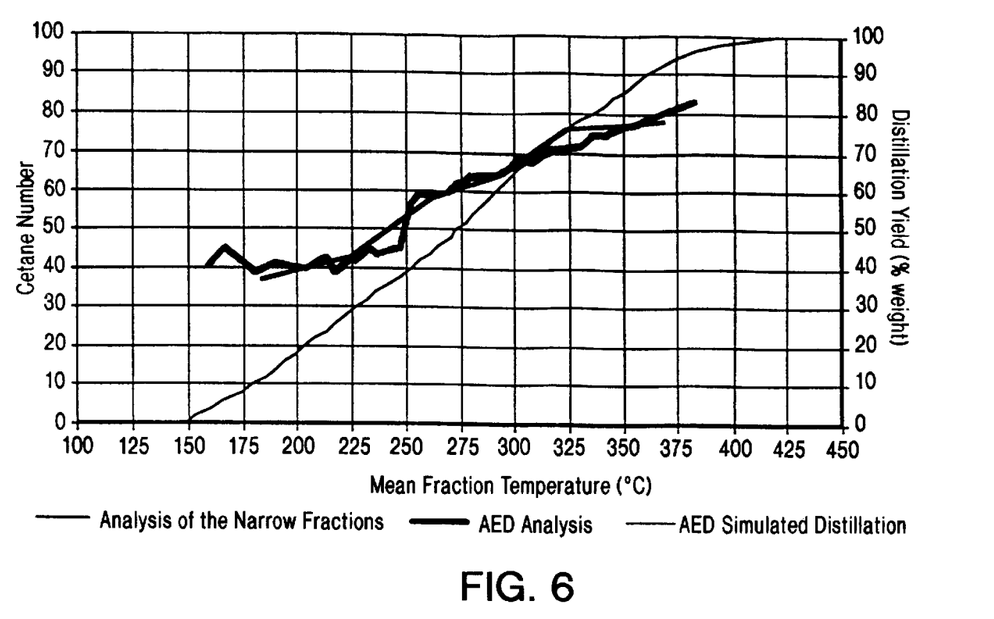

The results of the prediction of cetane number by GC-AED shown in FIG. 2 (cetane number that is calculated as a function of the cetane number that is measured by CFR engine) in Table 8.

TABLE 8

Examples predicting the Cetane Index of the Distillate by GC-AED

| Ref. | Measured | Predicted | Ref. | Measured | Predicted |
|---|---|---|---|---|---|
| 3 | 61.8 | 59.1 | 27 | 41.1 | 41.1 |
| 4 | 42.4 | 42.9 | 29 | 40.2 | 44.4 |
| 5 | 52.8 | 50.4 | 32 | 52.5 | 53.0 |
| 6 | 54.7 | 57.2 | 33 | 53.1 | 50.6 |
| 8 | 43.7 | 46.5 | 34 | 48.4 | 46.6 |
| 10 | 57 | 54.0 | 36 | 46.4 | 44.8 |
| 13 | 44.1 | 44.2 | 38 | 52.4 | 57.3 |
| 14 | 21.5 | 19.8 | 40 | 44.3 | 46.0 |
| 15 | 28 | 27.5 | 41 | 45.2 | 45.2 |
| 17 | 42.4 | 44.4 | 42 | 57.5 | 57.1 |
| 20 | 50.6 | 52.1 | 43 | 55.5 | 57.2 |
| 22 | 43.6 | 44.7 | 45 | 55.8 | 53.2 |
| 23 | 19.5 | 21.4 | 46 | 62.6 | 58.6 |
| 24 | 23.1 | 21.8 | 47 | 65.5 | 64.0 |
| 26 | 24.7 | 24.0 | 48 | 63.2 | 62.0 | structural datum in the case of such complex mixtures and can therefore be correlated with certain petroleum properties.

Through the example of cetane number, which is one of the most important properties of gas oils, it was also shown that it was possible to predict the changes, as a function of the distillation profile, of properties that are related to the mean distillate structure. This application is particularly useful for optimizing the distillation intervals of the petroleum fractions as a function of the desired specifications and for more finely analyzing the effect of the operating conditions on the quality of the effluents of a process.

As an example, FIGS. 3 to 6 depict the GC-AED cetane profile compared to the cetane profile that is determined by an engine in the narrow fractions that are obtained by preparative distillation on a catalytic cracking gas oil, hydrodemetalization gas oil, atmospheric-distillation gas oil, and hydrocracking gas oil. GC-AED analysis therefore makes it possible to determine the cetane number for a given distillation fraction and to know, simultaneously, its yield.

EXAMPLE 2

Determination of the Percentage of Global Aromatic Carbon and Distillation Profile This analysis makes it possible to track the variation of the aromatic carbon content, and it can be correlated with the hydrogen consumption of the refining processes to optimize the economy of the process.

The aromatic carbon content is usually determined by nuclear magnetic resonance of the carbon (ASTM D5292); it can also be calculated within the framework of correlative ndM methods (ASTM D3238).

Figure 7:
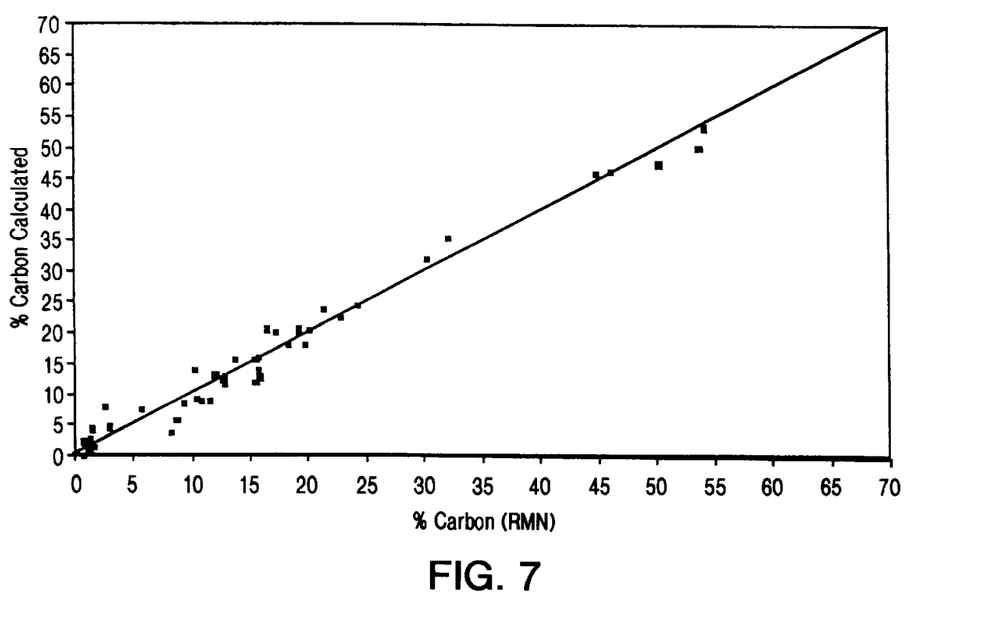
FIG. 7 shows the parity diagram for the aromatic carbon (% m/m)
Figure 8:
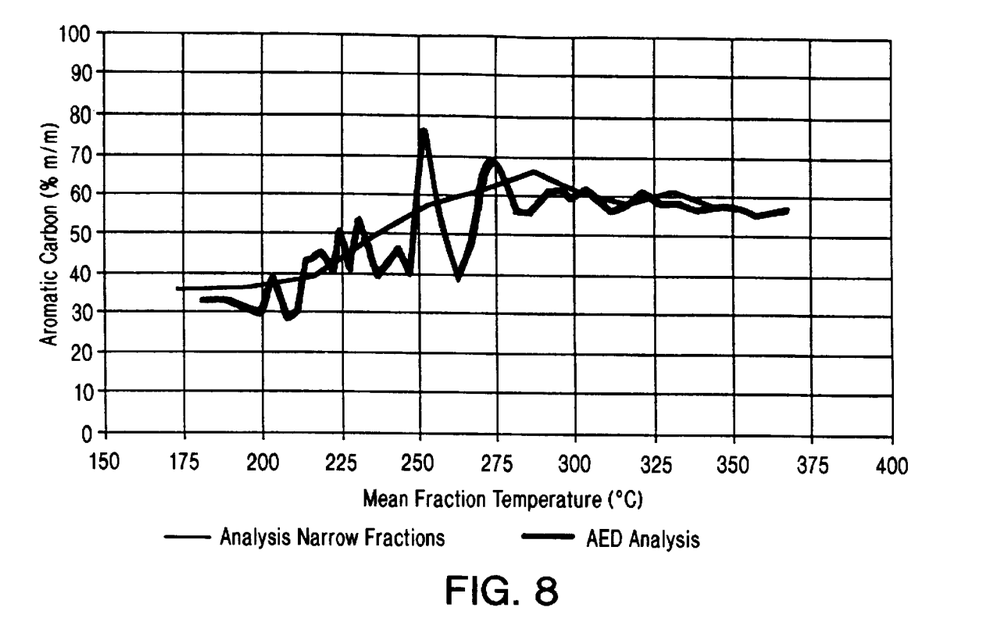
FIGS. 8 and 9 show the aromatic carbon profile (% m/m) as a function of the mean fraction temperatures of gas oils of different structures.
Figure 9:
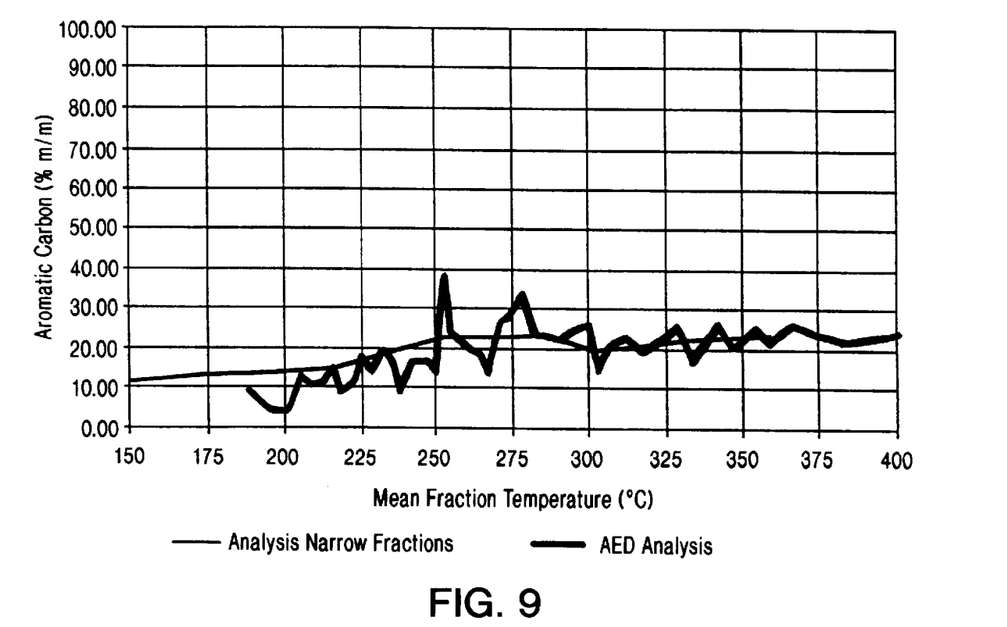

The results of the prediction of the aromatic carbon percentage by GC-AED are depicted in FIG. 7. As an example, in FIGS. 8 and 9, the GC-AED aromatic carbon percentage profile, compared to that determined by the reference method by NMR on the narrow fractions that are obtained by preparative distillation on a catalytic cracking gas oil (ref 14) and an atmospheric-distillation gas oil (ref 4), are depicted. The GC-AED analysis therefore makes it possible to determine the percentage of aromatic carbon for a given distillation fraction and to know, simultaneously, its yield.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for determining at least one of the following physico-chemical properties of a petroleum fraction:

density;

the refraction index;

the elementary composition of the distillation profile;

the simulated distillation curve of the product (%(m/m)= f(T° C.));

a cold property;

data relating to the concentrations of different radicals and their distribution as a function of the boiling point of the product;

the aniline point;

the smoke point;

the percentage % (m/m) of aromatic carbon Ca;

the percentage % (m/m) of paraffinic carbon Cp;

the percentage % (m/m) of naphthenic carbon Cn;

the cetane number; which comprises:

a) carrying out at least one conventional analysis of a set of reference petroleum samples to determine a first set of data of a calculation matrix for developing a correlative model;

b) analyzing each reference petroleum sample by chromatography, coupled to at least one detector under suitable conditions, to determine the distribution of at least one element selected from carbon, hydrogen, sulfur, and nitrogen as a function of the boiling points of the components of the sample, and determine a second set of data of the calculation matrix;

c) determine different coefficients of the correlative model from the first and second sets of data according to a multivaried method of analysis;

d) conducting chromatographic analysis of said petroleum fraction under the same conditions as those of step (b) to determine the distribution of at least one element of the carbon, hydrogen, sulfur, and nitrogen group as a function of the boiling points, to determine a third set of data relating to the petroleum fraction;

e) multiplying the third set of data of step (d) by the different coefficients of the correlative model; and f) determining the physico-chemical property that is derived from the petroleum fraction as a function of the boiling points of its components.

2. The method of claim 1, wherein the distribution of the element hydrogen is determined in step (b).

3. The method of claim 1, wherein the distribution of the element carbon is determined in step (b).

4. The method of claim 1, wherein the detector is a mass spectrometer.

5. The method of claim 1, wherein the detector is an atomic emission detector.

6. The method of claim 1, wherein the chromatography is gas chromatography.

7. The method of claim 6, wherein preparative liquid chromatography is carried out upstream from the gas chromatography.

8. The method of claim 6, wherein the gas chromatography is capillary column gas chromatography.

9. The method of claim 1, wherein the cetane number is one of the physico-chemical properties determined.

10. The method of claim 1, wherein the conventional analysis in step (a) includes mass spectrometry, flame ionization detection, specific detection of sulfur or nitrogen or atomic emission detection.

11. The method of claim 1, wherein the multivaried method of analysis in step (c) includes partial least square regression, principal component regression, a topological approach or a neural net.

12. The method of claim 1, further comprising using the determined physico-chemical properties to determine the cutpoints of products in a refining or other petrochemical process.

13. The method of claim 1, wherein the petroleum fraction has a boiling point less than 700° C.

14. The method of claim 1, wherein the petroleum fraction is a distillate from a catalytic cracking process or a gas oil.

15. The method of claim 1, wherein the petroleum fraction is a distillate from catalytic cracking of low-test gasoline, light cycle oil or heavy cycle oil.

16. The method of claim 1, wherein the petroleum fraction is an atmospheric-distillation gas oil, a hydrotreated gas oil, a hydrocracking gas oil, a visbreaking gas oil, a hydrodemetalization gas oil, a hydrorefining gas oil or a kerosene.

* * * * *